(12) United States Patent
Hunter et al.

(10) Patent No.: US 7,258,810 B2
(45) Date of Patent: Aug. 21, 2007

(54) IN-SITU OXIDIZED TEXTURED SURFACES FOR PROSTHETIC DEVICES AND METHOD OF MAKING SAME

(75) Inventors: Gordon Hunter, Memphis, TN (US); Randy Fesmire, Memphis, TN (US); Harsh Gupta, Memphis, TN (US); Daniel Heuer, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 60 days.

(21) Appl. No.: 10/313,205

(22) Filed: Dec. 6, 2002

(65) Prior Publication Data

US 2003/0125808 A1    Jul. 3, 2003

Related U.S. Application Data

(60) Provisional application No. 60/338,420, filed on Dec. 6, 2001.

(51) Int. Cl.
   *B44C 1/22*    (2006.01)
   *C03C 15/00*   (2006.01)
   *C03C 25/68*   (2006.01)
   *C23F 1/00*    (2006.01)
(52) U.S. Cl. .................... 216/41; 216/42; 427/2.24; 427/2.26; 623/23.29; 623/23.5; 623/23.53
(58) Field of Classification Search ............ 623/23.5, 623/23.6, 16.11, 20.17, 23.29, 23.3, 23.31, 623/23.55; 427/2.24, 2.26; 216/100, 108, 216/40, 41, 42
See application file for complete search history.

(56) References Cited

U.S. PATENT DOCUMENTS

| 2,987,352 | A | | 6/1961 | Watson |
| 3,615,885 | A | | 10/1971 | Watson |
| 4,272,855 | A | | 6/1981 | Frey |
| 4,644,942 | A | | 2/1987 | Sump |
| 4,671,824 | A | | 6/1987 | Haygarth |
| 4,673,409 | A | | 6/1987 | Van Kampen |
| 4,746,532 | A | * | 5/1988 | Suzuki et al. ............... 428/336 |

(Continued)

FOREIGN PATENT DOCUMENTS

DE    19815598    10/1999

(Continued)

OTHER PUBLICATIONS

D'Lima, Darryl D., M.D., et al., *Bone Response to Implant Surface Morphology*, The Journal of Arthroplasty, vol. 13, No. 8, pp. 928-934 (1998).

(Continued)

*Primary Examiner*—Parviz Hassanzadeh
*Assistant Examiner*—Roberts Culbert
(74) *Attorney, Agent, or Firm*—Fulbright & Jaworski LLP (57) ABSTRACT

A textured surface and oxidation layer coating on a metallic material is accomplished through the chemical and/or electrochemical etching of the surface to modify the surface texture and an in-situ oxidation procedure. The surface is useful for the fabrication of prosthetic devices, particularly medical implants, due to the corrosion and wear resistance imparted by the oxidation layer and the ability to enhance grafting of the implant onto bone imparted by the surface texture.

12 Claims, 3 Drawing Sheets

U.S. PATENT DOCUMENTS

| | | | |
|---|---|---|---|
| 4,865,603 A | | 9/1989 | Noiles |
| 5,258,098 A | | 11/1993 | Wagner et al. |
| 5,354,390 A | | 10/1994 | Haszmann et al. |
| 5,415,704 A | | 5/1995 | Davidson |
| 5,456,723 A | * | 10/1995 | Steinemann et al. ..... 623/23.53 |
| 5,507,815 A | | 4/1996 | Wagner et al. |
| 5,571,017 A | * | 11/1996 | Niznick ....................... 433/174 |
| 5,843,289 A | | 12/1998 | Lee et al. |
| 5,922,029 A | | 7/1999 | Wagner et al. |
| 6,193,762 B1 | | 2/2001 | Wagner et al. |
| 6,554,793 B1 | | 4/2003 | Pauker et al. |
| 6,599,322 B1 | * | 7/2003 | Amrich et al. ............. 623/23.5 |

FOREIGN PATENT DOCUMENTS

| | | |
|---|---|---|
| WO | WO96/16611 | 6/1996 |
| WO | WO98/42390 | 10/1998 |
| WO | WO-01/54565 | 8/2001 |

OTHER PUBLICATIONS

Wong, M., et al., *Effect of surface topology on the osseointegration of implant materials in trabecular bone*, Journal of Biomedical Materials Research, vol. 29, 1567-1575 (1995).

International Search Report dated Apr. 10, 2003.

* cited by examiner

IN-SITU OXIDIZED TEXTURED SURFACES FOR PROSTHETIC DEVICES AND METHOD OF MAKING SAME

CROSS-REFERENCE TO RELATED APPLICATIONS

This application claims benefit of and priority to U.S. provisional patent application Ser. No. 60/338,420, filed Dec. 6, 2001.

TECHNICAL FIELD

The present invention relates generally to the field of orthopedic implants. Specifically, it is directed to orthopedic implants having texture-modified surfaces coated with a thin, dense, highly wear-resistant coating of diffusion hardened oxidation layer. Preferably, the texture modification is effected through chemical or electrochemical etching and the metallic implant comprises zirconium and the surface layer comprises oxidized zirconium. The surface coatings have an enhanced ability to promote bone in-growth. This invention also relates to methods for producing metallic orthopedic implants having texture-modified surfaces.

BACKGROUND OF THE INVENTION

Orthopedic implant materials must combine high strength, corrosion resistance and tissue compatibility. The longevity of the implant is of prime importance especially if the recipient of the implant is relatively young because it is desirable that the implant function for the complete lifetime of a patient. Because certain metal alloys have the required mechanical strength and biocompatibility, they are ideal candidates for the fabrication of prostheses. These alloys include 316L stainless steel, chrome-cobalt-molybdenum alloys and, more recently, titanium alloys which have proven to be the most suitable materials for the fabrication of load-bearing prostheses.

It has also been found that metal prostheses are not completely inert in the body. Body fluids act upon the metals causing them to slowly corrode by an ionizing process that thereby releases metal ions into the body. Metal ion release from the prosthesis is also related to the rate of wear of load bearing surfaces because the passive oxide film, which is formed on the surface, is constantly removed. The repassivation process constantly releases metal ions during the ionizing process. Furthermore, the presence of third-body wear (cement or bone debris) accelerates this process and microfretted metal particles increase friction.

The excellent corrosion resistance of zirconium has been known for many years. Zirconium displays excellent corrosion resistance in many aqueous and non-aqueous media and for this reason has seen an increased use in the chemical process industry and in medical applications. A limitation to the wide application of zirconium in these areas is its relatively low resistance to abrasion and its tendency to gall. This relatively low resistance to abrasion and the tendency to gall is also demonstrated in zirconium alloys.

U.S. Pat. No. 2,987,352 to Watson first disclosed a method of producing zirconium bearings with a specific form of oxidized zirconium as a surface layer. The method of Watson was refined by Haygarth (U.S. Pat. No. 4,671,824) resulting in improved abrasion resistance and better dimensional control of the oxidized product. The U.S. Pat. Nos. of Davidson (5,037,438; 5,152,794; 5,180,394; 5,370,694; 5,372,660; 5,496,359; and 5,549,667) demonstrated the many advantages that are realized through the use of the specific form of oxidized zirconium on zirconium and zirconium alloy substrates in prosthetic devices. These include increased strength, low friction and high wear resistance. U.S. Pat. No. 5,037,438 to Davidson first disclosed a method of producing zirconium alloy prostheses with an oxidized zirconium surface. The work of Watson and Davidson teach a specific form of oxidized zirconium which possesses all of the advantages of ceramic materials while maintaining the strength of metallic surfaces. The oxidation is characterized by the diffusion of free oxygen into the surface of the metal; the resulting oxide layer is characterized by the diffusion of free oxygen into the surface of the metal. The resulting "diffusion hardened" materials possess a unique combination of the advantageous properties of a ceramic and a metal, simultaneously minimizing the disadvantages of these materials. All of the U.S. patents cited above to Davidson, Watson, and Haygarth are incorporated by reference as though fully set forth herein. While the early work of Davidson focused on pure zirconium and alloys of zirconium in which zirconium was the predominant metal, later work has shown that this is not necessary in order to form the desired diffusion hardened oxide. For instance, an alloy of 74 wt % titanium, 13 wt % niobium and 13 wt % zirconium ("Ti-13-13") will form the diffusion hardened oxidation layer used herein. Ti-13-13 is taught in U.S. Pat. No. 5,169,567 to Davidson et al.

Another important performance criterion for medical implants is the degree of fixation stability. This is typically accomplished through ingrowth of surrounding tissue into the implant and its ability to become firmly anchored to other components such as bone cement with a large shear strength. A typical hip joint prosthesis includes a stem fixated into the femur, a femoral head, and an acetabular cup against which the femoral head articulates. A typical knee joint prosthesis has a femoral and tibial component, both of which are fixated to the respective bones. This is the stability with which the implant is anchored in place. This fixation could be to either bone or other tissue, or may consist, at least in part, of materials, such as bone cement, etc. The fixation stability of the prostheses of Davidson was realized in their use of porous metal beads or wire mesh coatings the promoted bone in-growth and increased surface area for adhesion to other materials. These techniques are taught in U.S. Pat. No. 5,037,438 and other patents of Davidson, and when combined with the advantages of oxidized zirconium, represented an improvement in performance of medical implants in numerous areas. Nevertheless, continued improvement in the fixation stability of such implants is desirable.

A principle goal in the field of prosthetic implants is the lengthening of the useful life of the implant such as to avoid or minimize the need for surgical revision or replacement. A delay or complete prevention of failure of an implant is desirable. The causes of implant failure are numerous. It is believed that the failures are attributable to the body's rejection of bone cement. It is also believed that rejection of bone cement is not the primary problem, but rather that bone cement is not a proper structural component for use as part of a joint implant because of its physical properties.

Specifically, natural bone has a modulus of elasticity of up to about $4 \times 10^6$ p.s.i. The metals used for implants generally have a modulus of elasticity on the order of $15\text{-}35 \times 10^6$ p.s.i. Polymethylmethacrylate (PMMA) cement, on the other hand, has a modulus of elasticity on the order of $0.3\text{-}0.5 \times 10^6$ p.s.i. The stiffness of PMMA cement is therefore less than either the metal prosthesis or the surrounding bone. Cement has lower mechanical properties strength and fatigue strength properties than does metal or bone. These comparative physical properties are thought to be the source of failure of hip and knee prostheses implanted using bone cement.

Prostheses may also be implanted without cement. These devices achieve fixation by in-growth of bone or tissue into the prosthesis or by wedging the prosthesis into bone. The devices may also include surface features which enhance ingrowth with fibrous tissue or bone. The surface features may be applied by deposition or spraying techniques.

It is generally understood that surface roughening results in increased surface area which typically leads to better adhesion for the fixation of two surfaces. Although a smooth surface minimizes the stresses within the implant, it also minimizes the total surface area. This decreased surface area significantly reduces the strength of the attachment of the implant to the bone and tissue, which is largely dependent upon the mechanical interaction of the implant and the tissue. This mechanical interaction is of two forms. One is a form of interlocking to the extent the tissue grows behind or around a part of the implant. The other is frictional, wherein the tissue grows into intimate approximation with the surface and results in a relatively tight frictional fit.

Wagner et al. have demonstrated a method in U.S. Pat. No. 5,922,029 (and the resulting product in U.S. Pat. No. 6,193,762) using an electrochemical etching techniques to create attachment surfaces having random irregular patterns that promote bone tissue ingrowth and also to facilitate joining of the surface to a second material. Wagner et al. teach analogous methods (U.S. Pat. No. 5,258,098) and medical implant products (U.S. Pat. No. 5,507,815) in which the etching methodology used is purely chemical. Although the techniques of Wagner et al. represent one potential source of methods for surface texture modification it is expected that any other surface texture modification techniques would be similarly useful in aiding fixation. For example, the teachings of Frey (U.S. Pat. No. 4,272,855), Van Kampen (U.S. Pat. No. 4,673,409, Sump (U.S. Pat. No. 4,644,942), and Noiles (U.S. Pat. No. 4,865,603), among others, can be combined with in situ diffusion hardened surface oxidation of Davidson to produce a prosthesis surface having the superior attributes of surface oxidation as well as the stabilization and in-growth enhancement benefits accruing from macroscopic texture modification.

There exists a need for a method to produce medical implants having improved fixation while preserving or improving the advancements realized through the use of oxidized zirconium. This improved stability is needed both with respect to the interface between the implant and bone and surrounding tissue as well as in the interface between the implant and other material such as bone cement. This should be accomplished while simultaneously preserving the advantages which inure through the use of in situ oxidized, diffusion hardened surfaces such as oxidized zirconium.

SUMMARY OF THE INVENTION

The invention is directed to a textured surface and oxidation layer coating on a substrate material and prosthetic devices of such textured surfaces and oxidation layer coatings.

In one aspect of the present invention, there is a method for producing an oxidized and textured surface layer on a metallic substrate which comprises modifying the texture of the surface of the substrate and oxidizing the surface to form a diffusion hardened surface on the metallic substrate.

The following are specific embodiments of the invention which, when used, may be used alone or in combination with other embodiments.

In a specific embodiment of the invention, the texture is modified by etching the surface with a chemical agent. The texture may also be modified by electrochemical etching. Preferably, the etching is performed using acid. Most preferably, the etching is performed through the application of a maskant layer to the surface of the metallic substrate. In a specific embodiment, the maskant is applied randomly. The maskant may be applied in a variety of ways, including but not limited to, spraying or sputtering of the maskant onto the surface of the metallic substrate. Preferably, when spraying or sputtering of the maskant is used, the maskant is applied randomly. In a specific embodiment, the step of applying a maskant to the surface of the metallic substrate is characterized by fully covering the surface with the maskant and thereafter partially removing a portion of the maskant. The partial removal of the maskant can be accomplished in any suitable way. Preferably, maskant removal is accomplished through laser ablation of a portion of the maskant. In another embodiment, mechanical etching may be used to modify the texture of at least a portion of the surface. In yet another embodiment, the texture modification is accomplished through the use of material deposition. Such material deposition preferably comprises chemical vapor deposition.

The oxidation step can be performed using air, steam, or water oxidation. Most preferably, oxygen is used as an oxidant. In an alternative embodiment, the oxidation method may comprise the use of a salt bath. In the preferred embodiment, the metallic substrate comprises zirconium or zirconium alloy. In other specific but non-limiting embodiments, the alloy may be (a) zirconium with up to about 4.5 percent by weight hafnium and up to about 3.0 percent by weight niobium; (b) zirconium with up to about 4.5 percent by weight hafnium; (c) zirconium with 2.5 to 2.8 percent by weight niobium; and (d) titanium with about 13 percent by weight niobium and about 13 percent by weight zirconium. The alloy may not contain any zirconium and may instead be comprised of metals such as hafnium, niobium, tantalum, and titanium.

In another aspect of the present invention, there is a prosthesis for implantation comprising a metallic prosthesis body having an implant portion, a bearing surface comprising at least one condyle on the prosthesis body, and a tibial component adapted to cooperate with the bearing surface and wherein at least a portion of the prosthesis body has a texture-modified surface, and wherein at least a portion of the surface of the prosthesis body comprises a diffusion hardened oxidation layer.

The following are specific embodiments which, when used, may be used alone or in combination with other embodiments.

In a specific embodiment, the tibial component comprises an organic polymer or a polymer based composite. In a preferred embodiment, the metallic prosthesis body is made of zirconium or zirconium alloy and the diffusion hardened oxidation layer is a blue-black or black oxidized zirconium. Preferably, the thickness of the diffusion hardened oxidation layer is preferably up to about 20 microns. Most preferably, the thickness of the diffusion hardened oxidation layer is up to about 10 microns.

In another embodiment, there is a prosthesis for implantation comprising a metallic prosthesis body for implantation into a femor having a head portion and a bearing surface on the head portion, the prosthesis also comprising an acetabular cup having an inner surface adapted to cooperate with the bearing surface on the head portion, wherein at least a portion of the surface of the metallic prosthesis body is texture-modified, and wherein at least a portion of the surface of the metallic prosthesis body comprises a diffusion hardened oxidation layer.

The following are specific embodiments which, when used, may be used alone or in combination with other embodiments.

In one embodiment, the inner surface of the acetabular cup comprises an organic polymer or a polymer based composite. In the preferred embodiment, the metallic prosthesis body is made of zirconium or zirconium alloy and the diffusion hardened oxidation layer is a blue-black or black oxidized zirconium. Preferably, the thickness of the diffusion hardened oxidation layer is up to about 20 microns. Most preferably, the thickness of the diffusion hardened oxidation layer is up to about 10 microns.

In another embodiment, a prosthesis for implantation in a patient comprises a metallic prosthesis body having an implant portion, a bearing surface on the prosthesis body which is sized and shaped to engage or cooperate with a second bearing surface on another implant portion; wherein at least a portion of the surface of the metallic prosthesis body is texture-modified, and wherein at least a portion of the surface of the metallic prosthesis body comprises a diffusion hardened oxidation layer.

The following are specific embodiments which, when used, may be used alone or in combination with other embodiments.

Preferably, the prosthesis has a metallic body comprising zirconium or zirconium alloy and the diffusion hardened oxidation layer is a thin blue-black or black oxidized zirconium. Preferably, the thickness of the diffusion hardened oxidation layer is up to about 20 microns. Most preferably, the thickness of the diffusion hardened oxidation layer is up to about 10 microns.

In another embodiment, there is prosthesis comprising a bearing surface and a counter-bearing surface adapted to cooperate with the bearing surface and wherein at least a portion of the surface of said prosthesis is texture-modified and wherein at least a portion of the surface of said prosthesis comprises a diffusion hardened oxidation layer.

The following are specific embodiments which, when used, may be used alone or in combination with other embodiments.

Preferably, the prosthesis comprises zirconium or zirconium alloy and the diffusion hardened oxidation layer is a blue-black or black oxidized zirconium layer. Preferably, the thickness of the diffusion hardened oxidation layer is up to about 20 microns. Most preferably, the thickness of the diffusion hardened oxidation layer is up to about 10 microns. In a specific embodiment, the prosthesis is a spinal prosthesis. Preferably, the spinal prosthesis comprises zirconium or zirconium alloy and the diffusion hardened oxidation layer is a blue-black or black oxidized zirconium layer. In another specific embodiment, the spinal prosthesis is a spinal disc prosthesis. Preferably, the spinal disc prosthesis comprises zirconium or zirconium alloy and the diffusion hardened oxidation layer is a blue-black or black oxidized zirconium layer.

There is also a medical implant for inserting into the body tissue of the patient comprising a component, where at least a portion of the surface of the component is texture-modified and where at least a portion of the surface of the component comprises a diffusion hardened oxidation layer. In further embodiments, the medical implant may include, but is not limited to, bone plates or bone screws.

The following are specific embodiments which, when used, may be used alone or in combination with other embodiments.

In a specific embodiment, the medical implant comprises zirconium or zirconium alloy and the diffusion hardened oxidation layer is a blue-black or black oxidized zirconium coating. In another embodiment, the diffusion hardened oxidation layer has a thickness of up to about 20 microns. In another embodiment, the diffusion hardened oxidation layer has a thickness of up to about 10 microns. The medical implant may further comprising a self-grafting device.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

As used herein, "a" or "an" may mean one or more. As used herein in the claim(s), when used in conjunction with the word "comprising", the words "a" or "an" may mean one or more than one. As used herein, "another" may mean at least a second or more.

As used herein, the term, "medical implant" includes any device for implantation into the body. It is broader than and inclusive of prosthetic devices and includes bone plates and bones screws and related devices.

As used herein, "metallic" may be a pure metal or an alloy.

As used herein, the term "texture modified" in reference to a surface is defined as a native surface which has been treated by techniques known in the art to enhance bone in-growth and on-growth to improve fixation stability. It does not include those methods which modify the native surface solely by the addition of extraneous material, either of the same or different composition as that of the native surface, such as by the incorporation of metal beads or wire mesh coatings to the native surface. These latter techniques merely cover the native surface and create a new surface for bone in-growth and on-growth, as opposed to texture-modifying native surface.

As used herein, "zirconium alloy" is defined as any metal alloy containing zirconium in any amount greater than zero. Thus, an alloy in which zirconium is a minor constituent is considered a "zirconium alloy" herein. Similarly, a "metal alloy" of any other named metal (e.g., a hafnium alloy or a niobium alloy; in these cases, the named metal is hafnium and niobium, respectively) is defined as any alloy containing the named metal in any amount greater than zero.

The following discussion contains illustrations and discussions of preferred embodiments for practicing the present invention. However, they are not limiting examples. Other examples and methods are possible in practicing the present invention.

The present invention relates to providing an enhanced attachment surface for an implantable prosthetic device. A texture-modified surface consisting of a regular pattern or an irregular surface is formed on at least a part of the overall surface of the prosthetic which is, or has been, surface oxidized using an in situ oxidation process which results in a diffusion hardened oxidation layer typically of a thickness of 20 microns or less. The present invention encompasses prosthetic devices in which the textured surface and the in situ, diffusion-hardened oxidized surface occupy, at least in part, the same surface area, as well as prosthetic devices in which the textured surface and the in situ diffusion-hardened oxidized surface occupy different and distinct surfaces of the prosthetic device. The only requirement is that the prosthetic device somewhere possesses both a textured surface and an in situ diffusion-hardened oxidized surface.

The inventors have discovered that the combination of in situ formed, diffusion hardened oxidation layers synergistically improves the performance of surface texture modification techniques.

Surface Texture Modification

Figure 1:
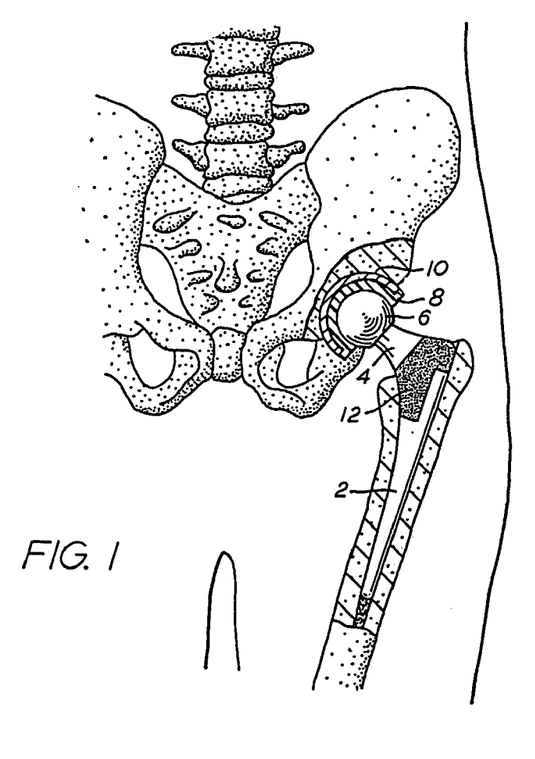
FIG. 1 is a schematic diagram depicting a hip joint prosthesis in position.
Figure 2:
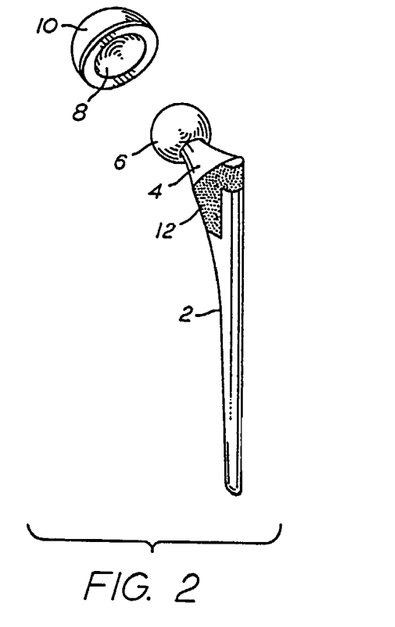
FIG. 2 is a schematic diagram showing a typical hip join prosthesis.

A typical hip joint prosthesis is shown in FIGS. 1 and 2. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to promote fixation of the implant by ingrowth of surrounding tissue into the porous coating. Similarly, such a porous metal bead or wire mesh coating can also be applied to the acetabular component. Importantly, area 12 may consist of a texture-modified area to accomplish the same objective as the porous metal bead or wire mesh coating.

Figure 3:
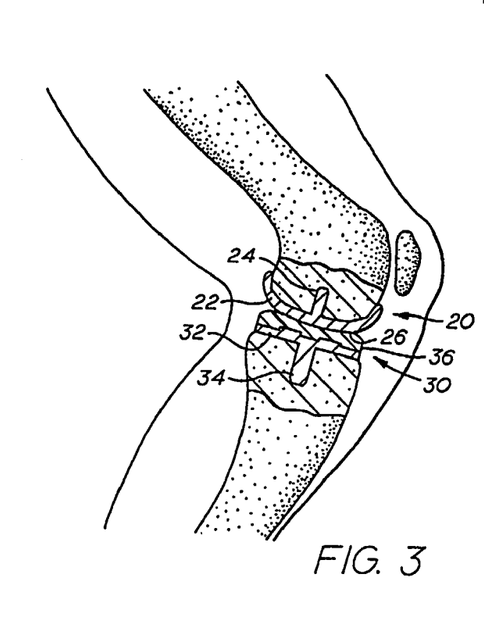
FIG. 3 is a schematic diagram of a knee joint prosthesis in place.
Figure 4:
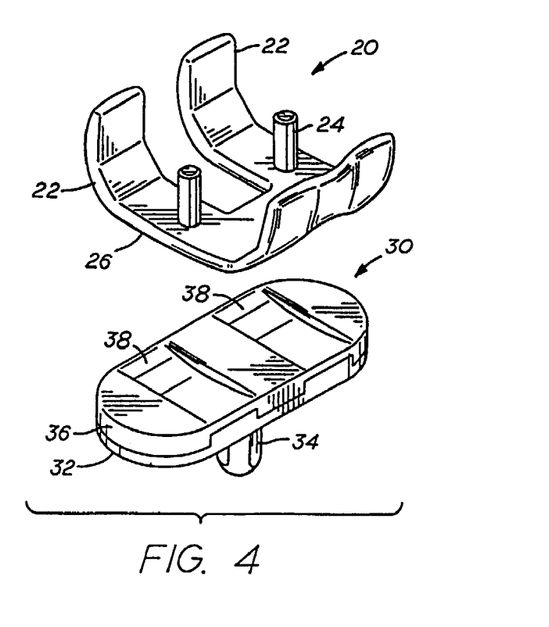
FIG. 4 is a schematic diagram of the parts of a typical knee joint.

A typical knee joint prosthesis is shown in FIGS. 3 and 4. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36 is mounted atop the tibial base 32 and is supplied with grooves 38 similar to the shape of the condyles 22. The tibial base, peg, and platform are ideal candidates for texture modification and diffusion hardened oxidation, as well as other portion of the knee prosthesis of FIG. 3.

The hip joint prostheses and knee joint prostheses explicitly described above are merely given as illustrative but non-exhaustive examples of prosthesis for which the present invention is applicable. It is understood by those of skill in the art that the present invention may be extended to other hip and knee joint prostheses, as well as other prostheses including, but not limited to, spine, shoulder, elbow, and finger prostheses. Examples of spinal applications would include spinal prostheses such as vertebral body replacements and spinal disc prostheses, as well as others. The invention is also applicable to medical implants generally including, including, but not limited to, bone plates and bone screws.

The most common methods of surface texture modification involve the use of maskants and chemical etchants. In such techniques, maskants are used to protect various portions of the surface from the application of a chemical etchant which only etches areas unprotected by the maskant. Where the invention employs chemical etching, the surface is prepared through an etching process which utilizes the random application of a maskant and subsequent etching of the metallic substrate in areas unprotected by the maskant. This etching process may be repeated a number of times as necessitated by the amount and nature of the irregularities required for any particular application, or it may be performed once. Control of etchant strength, and the process conditions of temperature and time permit operator control over the resulting surface produced by the process. The number of repetitions, and the particular maskant and etchant utilized for a given attachment surface is dictated by the base metal utilized for the implant. While a zirconium or zirconium alloy implant is contemplated as the best mode of practice in the invention, it is to be specifically understood that any metal substrate which is capable of being oxidized by the diffusion hardening in situ oxidation technique described in fuller detail below may be utilized as the implanted material. A change in the base metal may necessitate a change in the maskant and etchant. The use of other suitable substrate metals is within the scope of the present invention.

In the chemical etching embodiment, a maskant is applied to the surface to be etched in a random fashion. The random spattering of the maskant on the surface may be accomplished by, among other techniques, manually applying the maskant by brushing it using a brush or utilizing any type of fibrous applicator loaded with the maskant. Another method of application would be delivered in an air stream utilizing an air brush.

The maskant is selected to provide a substance that will cling tightly to the surface of the implant during manipulation of the implant and will also remain stable when the etchant solution is applied to the coated part. The maskant must also be removable residue-free after the etchant step(s) are completed. Examples of suitable maskants include, but are not limited to acrylic, epoxy, or polyester maskants. The maskant ideally produces sharply defined edges once the etching process has begun and not itself deteriorate during the etching process.

The surface of the implant must be clean and grease-free in preparation for the application of the maskant. Mechanical cleaning using a light abrasive blast of metal oxide particles, glass beads, or other suitable materials is preferred. Alternatively, grit blasting is possible. A solvent such as methanol may be utilized alone or with a blasting step. The maskant may be any material which is impervious to the etchant and may consist, at least in part, materials such as neoprene elastomers and alpha-olefin copolymers, dissolved in a carrier solvent. The particular maskant should be tailored to the type of etchant utilized. The viscosity of the maskant, may be increased by evaporation of the carrier. Thicker maskants typically produce superior results in terms of applying the maskant utilizing manual daubing or spray application techniques. It is to be specifically noted that the maskant is applied in a random spattered fashion allowing only a portion of the surface of the implant to be coated thereby. A random "polka dot" pattern is preferred in which each of the maskant points is of varying size and thickness when compared to the others. In some instances, the applied maskant may be partially abraded utilizing the grit blasting technique described previously for cleaning with an 80-120 mesh grit at 80-90 psi to assist in providing an irregular maskant coating.

Maskant features may differ depending upon the application. Maskant may be applied as thick agglomerations or as thin spots. It is desirable to achieve a variety of sizes and thicknesses of maskant in order to obtain the proper random finished surface. Each of these particular maskant surface features produces a somewhat different etched result. An optional step of drying the maskant at an elevated temperature may be useful. The conditions may vary depending upon the nature of the maskant, however, four to five minutes at 200° F. is usually sufficient.

While a number of etchants may be utilized, one particular embodiment utilizes a standard 30% nitric acid 6% hydrofluoric acid combination which is readily available. The etchant is applied at 110° F. for approximately 4 minutes to achieve a desired 0.008-0.010 inch etch depth. This time period or the strength of the etchant solution may be adjusted upwardly or downwardly to achieve a heavier or lighter etching. The etching is halted in a water bath or spray.

The maskant material may be removed in a variety of ways, including mechanically or chemically. Mechanical brushing or blasting of the maskant may be used to peel off the maskant in some cases. Additionally, the use of nitric acid is contemplated to dissolve the maskant material.

The above described surface treatment yields a number of surface features. Primary plateaus correspond to the more thickly applied maskant plateau. Heavy maskant coatings completely protect the implant surface, preventing any metallic material from being removed at this point. Secondary plateau corresponds to thinner maskant layers. Intermediate heights of the secondary plateaus are indicative of an area where the maskant performed for some period during the etching cycle but eventually failed before the etching cycle was complete, allowing some of the alloy to be etched away. The resulting surface also consists of gradually sloping surface features corresponding to a gradually tapering maskant coverage which partially protects the underlying substrate during the etching cycle. Highly sloped features indicate a thicker maskant coating which enjoyed a highly defined boundary before etching. Medium sloped features indicate a maskant condition intermediate the two previously described. The extremes of the etching are indicated by completely unetched areas and by those areas which illustrate the effect of complete maskant coating versus no maskant coating. One or more additional masking and etching cycles are possible resulting in patterns having analogous features superimposed on the previously formed surface. An increasing level of complexity of surface results from multiple applications of masking and etching cycles. A wide variety of different levels of depression and protrusion permit the ingrowth of bone and to allow for a firm anchoring of the bone along the surface of the implant structure. The surface features are irregularly shaped to promote bone ingrowth.

When using an electrochemical etching, the choice of maskant and the process parameters for a given surface is dictated by the substrate metal utilized for the implant. While a zirconium or zirconium alloy implant is contemplated as the best mode of practice in the invention, it is to be specifically understood that any base metal may be utilized as the implanted material. A change in the substrate metal may require the use of a different maskant electrolyte, and the process conditions of the electrochemical etching process. The use of other suitable substrate metals is within the scope of the present invention. Any suitable maskant and process conditions of the electrochemical etching process are also within the scope of the present invention.

After the maskant material has been applied, the exposed portion of the attachment surface of workpiece is ready to be electrochemically etched. The exposed portion of the attachment surface is that portion which is not covered by maskant deposits. A tank may be used to submerge the workpiece and the cathode under an electrolyte fluid. The workpiece is the anode of the electrochemical system and is connected to the positive terminal of a direct current power supply. The electrolyte fluid fills the work gap between the cathode and the attachment surface of the workpiece. The cathode should be of the same approximate dimensions of the workpiece such that a cathodic surface area is everywhere adjacent to the area on the workpiece to be etched. The electrolyte fluid is pumped at controlled rate through a passageway in the cathode and out through an orifice into the work gap between the cathode and the anode workpiece. The electrochemical hardware is known to those of skill in the art. A typical arrangement is more fully described in U.S. Pat. No. 5,922,029 to Wagner et al. which is fully incorporated by reference as though fully disclosed herein.

The electrolyte fluid for the electrochemically etching procedure is preferably a solution containing the proportions of one pound each of NaCl and $NaNO_3$ dissolved in one gallon of water. One skilled in the art of electrochemically etching metals will recognize and employ the appropriate electrolyte fluid to be used for the type of metal of a particular workpiece. Control of the flow rate of the electrolyte fluid through the work gap is important because the electrolyte fluid must adequately remove both the heat and the reaction products of the electrochemical process. The optimum flow rate level is related to the amount of current employed. Higher ratios of flow rate to current give better removal of heat and reaction products. For the electrochemical etching a cobalt-chromium alloy, for example, the electrolyte fluid should flow through the work gap 104 at a rate of about 0.15-0.5 gallons per minute per 100 amps and have a temperature of between about 100-130° F. One skilled in the art of electrochemically etching metals will be able to determine the proper values of these parameters to use with a particular application.

The cathode may be made from any material suitable for use in electrochemical etching such as copper, nickel, or an alloy of tungsten-copper. The cathode should be configured so that the work gap between the cathode and the attachment surface of the workpiece is substantially uniform. This is accomplished by making the cathode substantially conformal to the attachment surface. Preferably, the work gap is between about 0.020-0.250 inches, more particularly between about 0.060-0.120 inches. One skilled in the art of electrochemically etching metal will be able to determine the proper work gap to use for a particular application. A direct current voltage difference between the cathode and the attachment surface of between about 8 V-24 V and a specific amperage of at least about 50 amp/in$^2$ of exposed portion of the attachment surface are to be maintained during the electrochemical etching of a workpiece. Preferably, the direct current voltage difference between the cathode and the attachment surface is between about 12-18 V and the specific amperage is about 75-120 amps per square inch of exposed portion of the attachment surface. The values of these parameters for use with other materials are readily determinable by one skilled in the art of electrochemical etching metals. The stated conditions will produce a metal removal rate of about 0.003 inch/minute when the workpiece material is a cobalt-chromium alloy.

Preferably, the etching is performed until a desired etch depth of about 0.002-0.007 inches is achieved. The time period and other parameters of the electrochemical etching process, particularly the specific amperage, may be adjusted upwardly or downwardly to achieve a heavier or lighter etching. The electrochemical etching process is halted by removing the voltage difference between the cathode and the workpiece.

Preferably, the masking/electrochemical etching process is repeated three times, though useful attachment surfaces may be obtained through the use of fewer and more numerous cycles. The amount of material removed during each cycle is to be determined by the particular application. Preferably, substantially the same amount of material, as measured by depth of material removal, is removed in each cycle. When multiple masking/electrochemical etching cycles are employed, it is preferable that the attachment surface be blasted with 80 to 120 mesh alumina grit prior to the application of the maskant material so as to promote the adhesion of the maskant material.

Other variations on the general method of chemical and/or electrochemical etching are possible and within the scope of the present invention. For example, the description provided above involves the random application of maskant to the surface to be texture modified, resulting in a random and irregular surface. Alternatively, the maskant can be applied in a controlled manner in which a signature surface would result. Such a systematic signature surface may be comprised of a regular pattern or if may be irregular. This could be accomplished by the controlled application of maskant. Alternatively, the maskant may be applied in such a way as to completely cover the attachment surface, followed by the systematic and controlled removal of selected portions of the maskant to effect a surface having regions of varying coverage. Such controlled removal may occur by way of photo removal, such as, for example, laser ablation of deposited maskant. Alternatively, a chemical, electrochemical, or mechanical removal may be used. Additionally, the use of precisely controlled deposition could effect the final mask directly, obviating the need for partial removal of masking prior to etching. For example, chemical vapor deposition techniques, among other deposition techniques, may be used. A number of other variations are possible which are immediately obvious to one of ordinary skill in the art upon reading this disclosure. All of these variations are within the scope of the present invention.

The surface modifications of the present invention may also be used to produce surfaces that are self-grafting and which shear the surface of bone or other tissue upon implantation and pack the bone or tissue material into the implant to promote bone or tissue in-growth or on-growth. Presently known in-growth and on-growth surfaces (e.g., sintered beads, sintered wire mesh, plasma spray, etc.) are not designed for this and do not accomplish this. The enhanced fixation provides an ideal complement to the high wear resistance of diffusion hardened oxidized surfaces.

While present preferred embodiments of the invention are described, it is to be distinctly understood that the invention is not limited thereto but may be otherwise embodied and practiced within the scope of the following claims.

In Situ Formed, Diffusion Hardened Oxidation Layer

The invention provides metallic orthopedic implants or prostheses having in situ oxidized diffusion hardened surfaces and a metallic substrate and the texture-modified surfaces taught above. Preferably the metallic substrate is zirconium or zirconium alloy and the oxide layer is a diffusion hardened layer comprising blue-black or blue oxidized zirconium. Other metallic substrate, such as, but not limited to, hafnium, niobium, and tantalum, and alloys thereof, are amenable to forming the oxidation layer of the present invention. In the discussion that follows, the focus is on zirconium and zirconium alloys; however, the invention is not so limited.

In the case of oxidized zirconium it has been found that small amounts of zirconium are sufficient to yield the desired diffusion hardened oxidation layer. For example, the desired oxidation layer has been successfully formed on an alloy having 13% zirconium, 13% niobium with the remainder being titanium. Oxygen, niobium, and titanium include common alloying elements in the alloy with often times the presence of hafnium. Yttrium may also be alloyed with the zirconium to enhance the formation of a tougher, yttria-stabilized zirconium oxide coating during the oxidation of the alloy. While such zirconium containing alloys may be custom formulated by conventional methods known in the art of metallurgy, a number of suitable alloys are commercially available. These commercial alloys include among others Zircadyne 705, Zircadyne 702, and Zircalloy. Other non-limiting examples of alloys useful herein include zirconium with up to about 4.5 wt % hafnium and up to about 3.0 wt % niobium, zirconium with up to about 4.5 wt % hafnium, zirconium with about 2.5-2.8 wt % nioboium and up to about 4.5 wt % hafnium, and titanium with about 13 wt % niobium and 13 wt % zirconium. The presence of zirconium is not deemed necessary, as under similar oxidative conditions chemically similar metals such as hafnium, niobium, titanium, and tantalum and non-zirconium-containing alloys thereof may form the diffusion hardened oxidation layer of the present invention. All of these metals and metal alloys are within the scope of the present invention. The foregoing list is merely illustrative of metal and metal alloy candidates which may be used and is not exhaustive.

The base metal alloys are cast or machined by conventional methods to the shape and size desired to obtain a prosthesis substrate. he substrate is then subjected to process conditions which cause the natural in situ formation of a tightly adhered, diffusion-bonded coating of oxide layer on its surface. The process conditions include, for instance, air, steam, or water oxidation or oxidation in a salt bath. For zirconium and zirconium alloys, these processes ideally provide a thin, hard, dense, blue-black or black, low-friction wear-resistant zirconium oxide film or coating of thicknesses typically on the order of several microns ($10^{-6}$ meters) on the surface of the prosthesis substrate. Below this coating, diffused oxygen from the oxidation process increases the hardness and strength of the underlying substrate metal.

The air, steam and water oxidation processes are described in now-expired U.S. Pat. No. 2,987,352 to Watson, the teachings of which are incorporated by reference as though fully set forth. The air oxidation process provides a firmly adherent black or blue-black layer of zirconium oxide of highly oriented monoclinic crystalline form. If the oxidation process is continued to excess, the coating will whiten and separate from the metal substrate. The oxidation step may be conducted in either air, steam or hot water. For convenience, the metal prosthesis substrate may be placed in a furnace having an oxygen-containing atmosphere (such as air) and typically heated at 700°-1100° F. up to about 6 hours. However, other combinations of temperature and time are possible. When higher temperatures are employed, the oxidation time should be reduced to avoid the formation of the undesired oxide form. In the case of zirconium or zirconium alloys, the undesired oxide is the white oxide.

For zirconium and zirconium alloys, although larger thicknesses of up to about 20 microns may be used, it is preferred that a blue-black zirconium oxide layer ranging in thickness from about 1 to about 10 microns should be formed. For example, furnace air oxidation at 1000° F. for 3 hours will form an oxide coating on Zircadyne 705 about 4-5 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the prosthesis, will result. In general, thinner coatings (1-4 microns) have better attachment strength.

One of the salt-bath methods that may be used to apply the zirconium oxide coatings to the metal alloy prosthesis, is the method of U.S. Pat. No. 4,671,824 to Haygarth, the teachings of which are incorporated by reference as though fully set forth. In the case of zirconium or zirconium alloys, the salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt %. The addition of sodium carbonate lowers the melting point of the salt. As in air oxidation, the rate of oxidation is proportional to the temperature of the molten salt bath and the '824 patent prefers the range 550°-800° C. (1022°-1470° F.). However, the lower oxygen levels in the bath produce thinner coatings than for furnace air oxidation at the same time and temperature. A salt bath treatment at 1290° F. for four hours produces an oxide coating thickness of roughly 7 microns.

Whether air oxidation in a furnace or salt bath oxidation is used, the zirconium oxide coatings are quite similar in hardness. For example, if the surface of a wrought Zircadyne 705 (Zr, 2-3 wt. % Nb) prosthesis substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700-2000 Knoop hardness.

These diffusion-bonded, low friction, highly wear resistant oxide layer have heretofore been grown on the surfaces of orthopedic implants subject to conditions of wear. Such surfaces include, among others, the articulating surfaces of knee joints, elbows and hip joints. Hip and knee prostheses are illustrated schematically in FIGS. 1 and 2 (hip) and FIGS. 3 and 4 (knee). As mentioned before, in the case of hip joints, the femoral head and stem are typically fabricated of metal alloys while the acetabular cup may be fabricated from ceramics, metals or organic polymer-lined metals or ceramics. In the present disclosure, we teach the use of these surfaces on other portions of a prosthesis as well. In particular, when combined with texture-modification techniques, the resulting surface exhibits enhanced fixation performance. Bone and tissue in-growth into the prosthesis is enhanced, and the shear strength of the surface against bone, tissue and other materials, relative to conventional prosthetic surfaces, is also enhanced.

The usefulness of texture-modified, diffusion hardened oxide layer coated prosthesis is not limited to load bearing prostheses, especially joints, where both a high rate of wear may be encountered and fixation is expected to be a problem. Because the oxide layer coating is firmly bonded to the pure metal or alloy prosthesis substrate, it provides a barrier between the body fluids and the pure metal or alloy metal thereby preventing the corrosion of the alloy by the process of ionization and its associated metal ion release.

Performance of Texture-Modified, Diffusion Hardened Oxidation Layer Surfaces

Shear Strength

We have performed experiments comparing shear strength of various surfaces against bone cement of 1) texture-modified and diffusion hardened oxidized surfaces, 2) texture-modified and unoxidized surfaces, and 3) surfaces which are neither oxidized nor texture-modified. The results of this testing showed that an oxidized textured surface has a substantially improved average shear strength with bone cement over that of an unoxidized similarly textured surface.

In the data below, "Textured Surface No. 1" was formed using a procedure in which the surface is completely covered with maskant, followed by the controlled laser ablation to partially remove some maskant, yielding the masked surface. This surface was then chemically etched using a nitric acid/hydrofluoric acid mixture. The remaining maskant was then removed and the surface was cleaned. "Textured Surface No. 2" was produced using a random spattering technique to apply the maskant and a nitric acid/hydrofluoric acid mixture as the etchant. In all cases, the substrate was a zirconium alloy containing 2.5% niobium.

The average shear strength of an oxidized Textured Surface No. 1 was nearly 500 p.s.i. greater than the corresponding unoxidized textured Surface No. 1, and the average oxidized Textured Surface No. 2 was more than 160 psi greater than the unoxidized Textured Surface No. 2. Also, in one of the unoxidized Textured Surface No. 1 specimens, some of the metal asperities were found to have sheared off during testing and remained embedded in the cement. This was not observed in any of the oxidized specimens. It appears that improved shear strength against bone cement and resistance to shearing of the texture features might be additional benefits to a diffusion hardened oxidized surface. The date is given below and shown graphically in FIG. 5.

Figure 5:
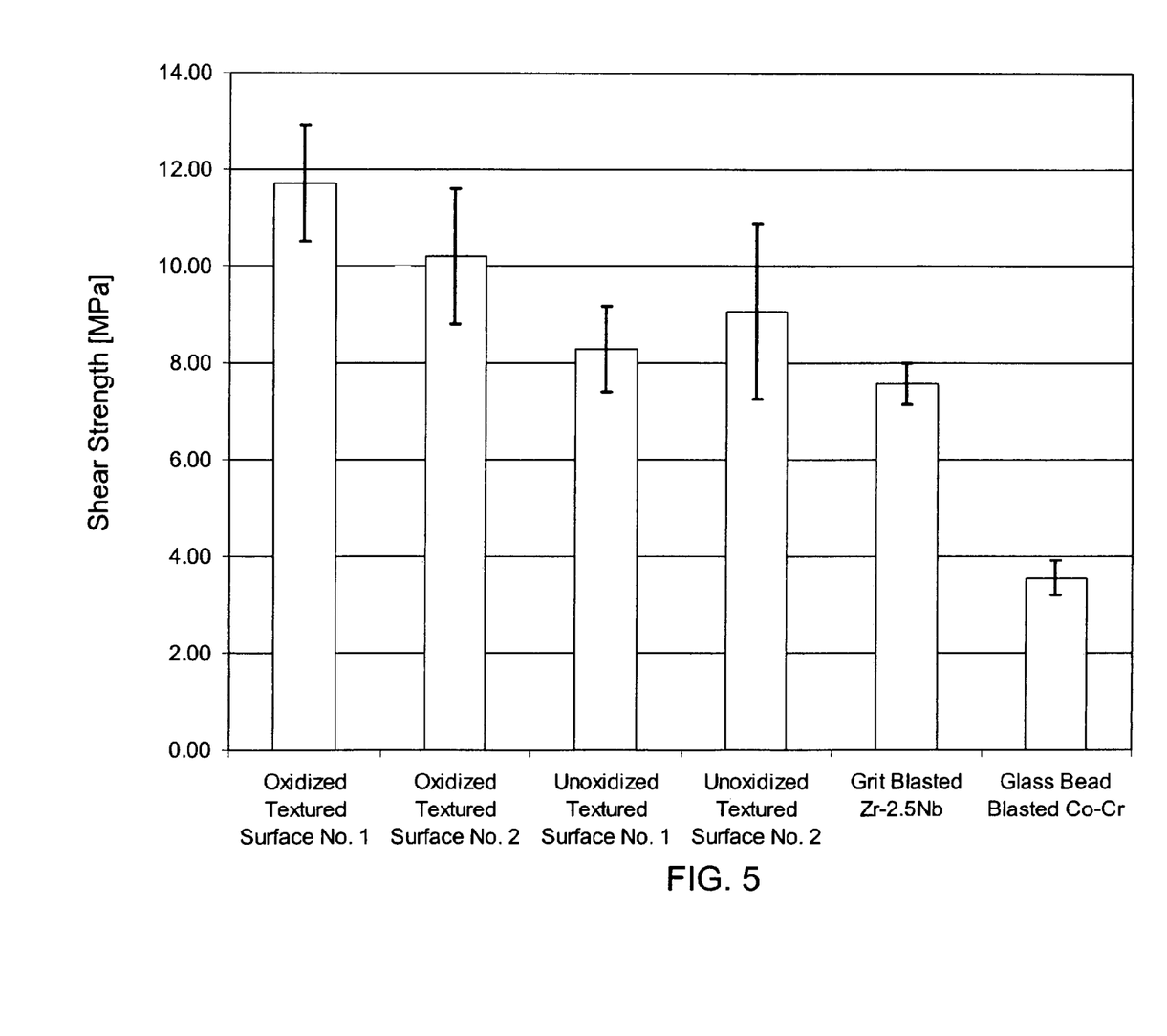
FIG. 5 graphically shows the Shear Strength of various surfaces.

| TEXTURE | SPECIMEN NO. | MATERIAL | OXIDATION CONDITION | SHEAR STRENGTH [MPA] | [PSI] |
|---|---|---|---|---|---|
| Textured | 451-4-1 | Zr-2.5Nb | Oxidized | 11.55 | 1675 |
| Surface | 451-4-2 | | | 12.31 | 1785 |
| No. 1 | 451-4-3 | | | 10.74 | 1557 |
| | 451-4-4 | | | 12.30 | 1784 |
| | 451-4-5 | | | 13.37 | 1939 |
| | 451-4-6 | | | 10.05 | 1458 |
| Average | | | | 11.72 | 1700 |
| S.D. | | | | 1.20 | 174 |
| Textured | 451-5-1 | Zr-2.5Nb | Oxidized | 9.94 | 1442 |
| Surface | 451-5-2 | | | 9.62 | 1395 |
| No. 2 | 451-5-3 | | | 10.35 | 1501 |
| | 451-5-4 | | | 10.54 | 1529 |
| | 451-5-5 | | | 8.25 | 1197 |
| | 451-5-6 | | | 12.55 | 1820 |
| Average | | | | 10.21 | 1481 |
| S.D. | | | | 1.40 | 204 |
| Textured | 451-6-1 | Zr-2.5Nb | Unoxidized | 8.81 | 1278 |
| Surface | 451-6-2 | | | 8.92 | 1294 |
| No. 1 | 451-6-3 | | | 8.25 | 1196 |
| | 451-6-4 | | | 9.19 | 1333 |
| | 451-6-5 | | | 7.78 | 1129 |
| | 451-6-6 | | | 6.79 | 985 |
| Average | | | | 8.29 | 1203 |
| S.D. | | | | .89 | 130 |
| Textured | 451-7-1 | Zr-2.5Nb | Unoxidized | 7.64 | 1108 |
| Surface | 451-7-2 | | | 8.92 | 1294 |
| No. 2 | 451-7-3 | | | 12.14 | 1761 |
| | 451-7-4 | | | 8.61 | 1249 |
| | 451-7-5 | | | 6.93 | 1005* |
| | 451-7-6 | | | 8.04 | 1166 |
| Average | | | | 9.07 | 1316 |
| S.D. | | | | 1.82 | 264 |
| Grit-Blasted; | 1LSZ/2LSZ (front) | Zr-2.5Nb | Unoxidized | 7.38 | 1071 |
| No Other | 3LSZ/4LSZ (front) | | | 7.81 | 1133 |
| Texture | 5LSZ/6LSZ (front) | | | 8.16 | 1183 |
| Modification | 1LSZ/2LSZ (back) | | | 7.79 | 1130 |
| | 3LSZ/4LSZ (back) | | | 7.35 | 1066 |
| | 5LSZ/6LSZ (back) | | | 6.96 | 1009 |
| Average | | | | 7.58 | 1099 |
| S.D. | | | | 0.43 | 62 |
| Bead-Blasted; | 269-193/269-202 | Co-Cr | N/A | 3.74 | 542 |
| No Other | 269-199/269-204 | | | 3.01 | 436 |
| Texture | 269-191/269-203 | | | 3.92 | 568 |
| Modification | 269-196/269-205 | | | 3.40 | 493 |
| | 269-197/269-201 | | | 3.72 | 540 |
| Average | | | | 3.56 | 516 |
| S.D. | | | | 0.36 | 52 |

*Inadequate cement layer - data not included in final analysis.

The oxidation process hardens the textured surface and it is believed that this allows it to act as rasp as the implant is impacted, grinding the cut surfaces of the bone and self-grafting the implant. The presence of freshly grated bone is thought to promote bone growth onto the textured surface. The unoxidized texture, being more ductile and not as hard, would not be as efficient in grinding the cut surfaces of the bone in this manner. An additional advantage can be seen in the data. The results demonstrate that an oxidized textured surface has a substantially improved average shear strength with bone cement over that of an unoxidized similarly textured surface.

In-Vivo Ovine Studies

In this study, an ovine animal model was used to determine the in vivo biological response to these macro-textured and oxidized zirconium surfaces and the resulting shear strengths they provide. A texturing method known commercially as ChemTex® 5-5-5 (CYCAM, Inc., Houston, Pa.), and a newly developed chemical texturing process known commercially as Tecotex® I-103 (Tecomet, Woburn, Mass.), were selected to produce macro-textured surfaces ($R_{max}$>0.4 mm) on a zirconium alloy (Zr-2.5Nb). These textured surfaces are subsequently oxidized to form a hard ceramic layer uniformly about 5 µm thick over the entire surface which consists predominantly of monoclinic zirconia.

The ChemTex® textured and oxidized zirconium (CT-OZ) surfaces and the Tecotex® textured and oxidized zirconium (TT-OZ) surfaces were compared to sintered Co—Cr beads (SB-CC), a common fixation surface for hip stem and knee femoral components, and ChemTex® textured Ti-6Al-4V (CT-Ti) surfaces, which have been used clinically on total hip replacement components. Also investigated was a ChemTex® textured zirconium surface left unoxidized (CT-Zr). Twelve cylindrical pin coupons (6.5 mm×15 mm) with each of the five surface types listed above were created. Each coupon was implanted into a 6.4-mm hole drilled in the lateral side of the distal metaphysis of an ovine femur, with one pin implanted per animal. Four sheep with each coupon type were given bone labeling solutions at two periods post-operatively. Solutions of calcein (15 mg/kg) and oxytetracycline (15 mg/kg) were administered intravenously at days 14 and 35 post-op, respectively. At six weeks post-op, the animals were euthanized and the femora were harvested.

The eight specimens of each type from the animals not given the bone labels were prepared for pin push-out testing. First, the boney tissue immediately adjacent to the ends of the pin was sectioned away, leaving bone in contact only with the intended test surfaces of the pin and producing flat bone surfaces perpendicular to the axis of the pin. An Instron 8511 servo-hydraulic mechanical testing frame (Instron Corporation, Canton, Mass.) was then used to apply a load to the medial end of the pin along its axis via a steel plunger 4.5 mm in diameter. A restricter plate was used to support the bone surrounding the lateral end of the pin. The load was increased at a displacement rate of 0.1 mm/s, and the maximum force required to dislodge the pin was recorded.

Statistical analysis of the push-out loads was performed using a one-way analysis of variance (ANOVA). Significant differences between groups were determined using a 95% confidence interval (p<0.05). The remaining four specimens of each type from the animals which had been given the bone labels were isolated with a minimum of 5 mm of bone left surrounding the pins. The bone/coupon specimens were then fixed for 1 week in 70% ethanol at 4° C., dehydrated through a series of graded alcohols, and cleared with chloroform using a Tissue-Tek VIP processor. The specimens were embedded in methyl methacrylate (MMA), and sectioned transversely using a diamond saw. "Cortical" and "medullary" sections were taken approximately 4 mm from the corresponding ends of the pin and ground to a minimum thickness of 50 μm. The sections were light green stained to identify bone in the histological sections.

Figure 6:
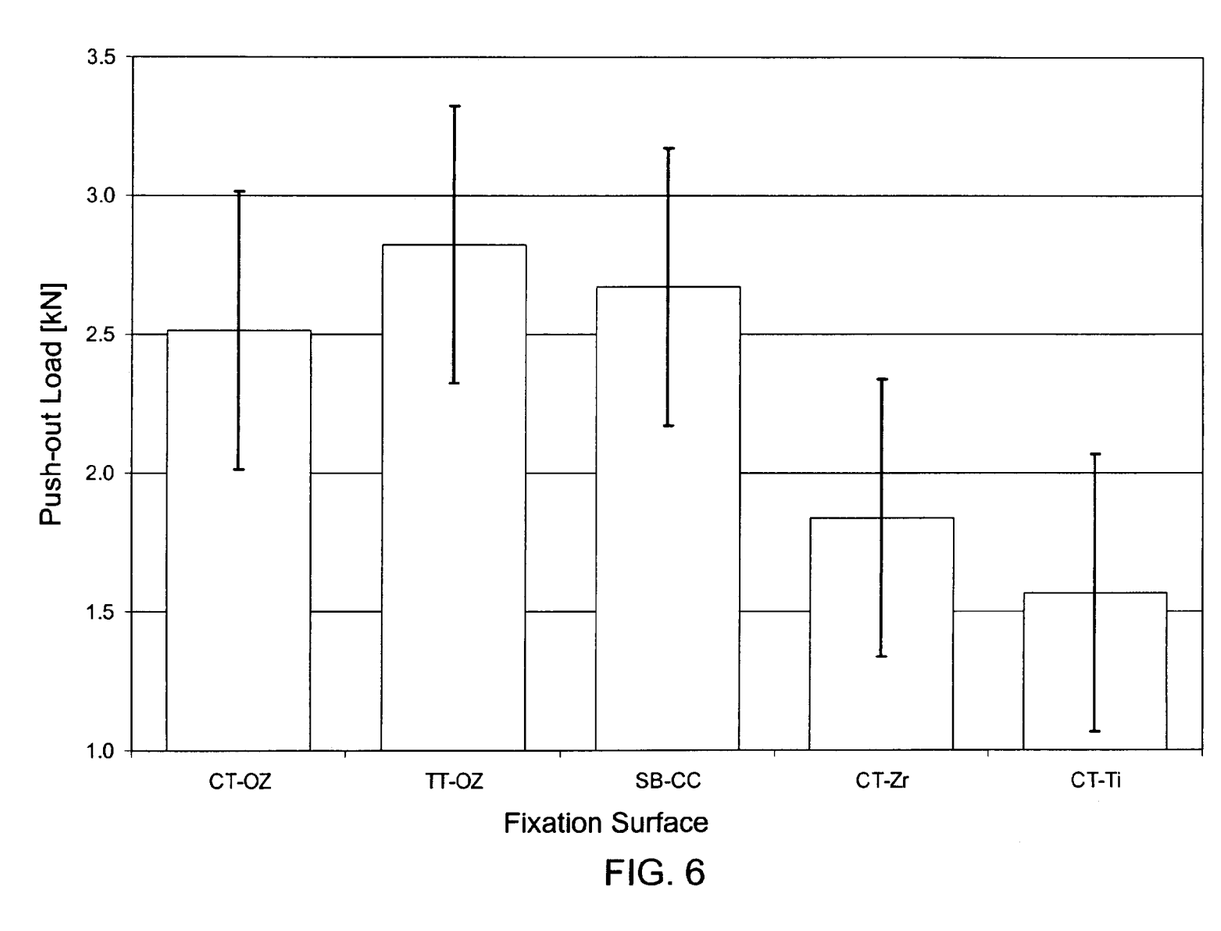
FIG. 6 graphically shows the results of pin push-out testing for various surfaces.

Pin push-out testing resulted in average push-out loads as shown in FIG. 6. The TT-OZ coupons produced the highest average push-out strength (2.83 kN), but this was not significantly different than that of the SB-CC (p=0.53) and CT-OZ (p=0.25) coupons. All three, however, withstood significantly higher push-out loads than the CT-Zr (p<0.04) and CT-Ti (p<0.008) surfaces. No significant difference between the CT-Zr and the CT-Ti surfaces (p=0.392) was found. Histological analysis showed bone growth in direct apposition to all five surfaces. For each, bone grew down to the deepest recesses of the fixation surface, providing mechanical interdigitation between the bone and the implant. The bone labels indicated that bone deposition had been initiated by day 14 post-op and was continuing at day 35 post-op for all of the surfaces investigated.

The macro-textured and oxidized zirconium surfaces (CT-OZ and TT-OZ) provided biological fixation strengths equivalent to those of sintered Co—Cr bead-coated surfaces (SB-CC). These results, along with the histological finding of active bone growth in direct apposition to the surfaces, suggest that both forms of macro-textured and oxidized zirconium surfaces should provide a clinical fixation equivalent to that of sintered Co—Cr beads.

All three of the above surfaces demonstrated significantly greater biological fixation strengths than chemically textured Zr-2.5Nb (CT-Zr) and Ti-6Al-4V (CT-Ti) surfaces. Of note is the improvement in the shear strength due solely to oxidation of the zirconium alloy. Both the CT-OZ and the CT-Zr pin coupons were made using the same Zr-2.5Nb alloy and were chemically textured in an identical manner, yet the first group, which was oxidized after the texturing process, produced a significantly higher biological fixation strength than the second group, which was left in the unoxidized condition.

The reasons for the improvement in performance with oxidation are not fully understood, but could be the result of several different factors. In a macrotextured oxidized zirconium knee femoral study, the hardened ceramic texture was observed to "shave" the prepared surface of the bone, forcing bone particles into the recesses of the texture. This may act in a "self-grafting" manner to encourage bone growth onto the implant surface. The softer textured metal surface may be less proficient in creating this effect, while the hard ceramic surface acts to reinforce the texture asperities and make them more resistant to abrasion by the bone. In addition, ceramic surfaces are resistant to corrosion and ion release, which could have some effect on the biological tissue immediately adjacent to the surface. By whatever means, the results suggest that oxidation of a textured zirconium surface significantly improves the biological fixation strength attainable.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

U.S. Patent Documents:

| | | |
|---|---|---|
| 2,987,352 | June 1961 | Watson |
| 4,671,824 | June 1987 | Haygarth |
| 4,673,409 | June 1987 | Van Kampen |
| 4,644,942 | February 1987 | Sump |
| 4,272,855 | June 1981 | Frey |
| 4,865,603 | September 1989 | Noiles |
| 5,922,029 | July 1999 | Wagner et al. |
| 5,507,815 | April 1996 | Wagner et al. |
| 5,258,098 | November 1993 | Wagner et al. |
| 6,193,762 | February 2001 | Wagner et al. |
| 5,037,438 | August 1991 | Davidson |
| 5,152,794 | October 1992 | Davidson |
| 5,169,597 | December 1992 | Davidson et al. |
| 5,180,394 | January 1993 | Davidson |
| 5,370,694 | December 1994 | Davidson |
| 5,372,660 | December 1994 | Davidson et al. |
| 5,496,359 | March 1996 | Davidson |
| 5,549,667 | August 1996 | Davidson |

Other References:
ASTM Manual on Zirconium and Hafnium, J. H. Schemel; Special Technical Publication 639, American Society for Testing and Materials, Philadelphia, Pa., 1977.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

What is claimed is:

1. A method of producing a modified surface on a metallic medical implant comprising the steps of: modifying the texture of at least a portion of the surface of said metallic medical implant to a roughness of $R_{max}$ of about 0.4 mm or greater to form a texture-modified surface; and, oxidizing at least a portion of the texture-modified surface of said metallic medical implant to form a texture-modified, diffusion hardened surface on said metallic medical implant.

2. The method of claim 1 wherein said step of modifying comprises a chemical or electrochemical etching.

3. The method of claim 2 wherein said etching comprises etching with acid.

4. The method of claim 2 wherein said etching comprises the further step of applying a maskant to the surface of the metallic medical implant.

5. The method of claim 4 wherein the maskant is randomly applied.

6. The method of claim 4 wherein said step of applying a maskant comprises the step of spraying or sputtering of maskant onto said surface of said metallic medical implant.

7. The method of claim 6 wherein said step of spraying or sputtering comprises a random application of maskant.

8. The method of claim 4 wherein said step of applying a maskant to the surface of the metallic medical implant is characterized by fully covering said surface with said maskant and thereafter partially removing a portion of said maskant.

9. The method of claim 8 wherein said step of partially removing comprises the step of laser ablating a portion of said maskant.

10. The method of claim 1, wherein said step of oxidizing comprises air, steam, or water oxidation processes.

11. The method of claim 1, wherein the metallic surface comprises zirconium or zirconium alloy.

12. The method of claim 11 wherein said zirconium alloy is selected from the group consisting of: zirconium with up to about 4.5 percent by weight hafnium and up to about 3.0 percent by weight niobium; zirconium with up to about 4.5 percent by weight hafnium; zirconium with 2.5 to 2.8 percent by weight niobium; and; titanium with about 13 percent by weight niobium and about 13 percent by weight zirconium.

* * * * *